(12) United States Patent
Rowles

(10) Patent No.: US 10,688,191 B2
(45) Date of Patent: Jun. 23, 2020

(54) DELIVERY OF A CHEMOTHERAPY AGENT ACROSS THE BLOOD-BRAIN BARRIER

(71) Applicant: Heidi Rowles, Goshen, OH (US)

(72) Inventor: Heidi Rowles, Goshen, OH (US)

(73) Assignee: HR BIOMED, LLC, Goshen, OH (US)

( * ) Notice: Subject to any disclaimer, the term of this patent is extended or adjusted under 35 U.S.C. 154(b) by 32 days.

(21) Appl. No.: 15/875,114

(22) Filed: Jan. 19, 2018

(65) Prior Publication Data

US 2019/0224327 A1    Jul. 25, 2019

(51) Int. Cl.
| | | |
|---|---|---|
| *A61K 47/55* | (2017.01) | |
| *A61P 35/00* | (2006.01) | |
| *A61K 31/352* | (2006.01) | |
| *A61K 31/17* | (2006.01) | |
| *A61K 47/54* | (2017.01) | |

(52) U.S. Cl.
CPC .............. *A61K 47/55* (2017.08); *A61K 31/17* (2013.01); *A61K 31/352* (2013.01); *A61K 47/545* (2017.08); *A61P 35/00* (2018.01)

(58) Field of Classification Search
CPC ..................................................... A61K 47/55
See application file for complete search history.

(56) References Cited

U.S. PATENT DOCUMENTS

| | | | |
|---|---|---|---|
| 2,419,937 A | 5/1947 | Adams | |
| 4,540,564 A | 9/1985 | Bodor | |
| 5,624,894 A | 4/1997 | Bodor | |
| 6,630,507 B1 | 10/2003 | Hampson et al. | |
| 7,001,991 B2 | 2/2006 | Faulk | |
| 7,557,182 B2 | 7/2009 | Beliveau et al. | |
| 8,632,825 B2 | 1/2014 | Velasco Diez et al. | |
| 8,729,029 B2 | 5/2014 | Khrestchatisky et al. | |
| 8,748,567 B2 | 6/2014 | Narasimhaswamy et al. | |
| 8,790,719 B2 | 7/2014 | Parolaro et al. | |
| 8,828,949 B2 | 9/2014 | Beliveau et al. | |
| 8,877,716 B2 | 11/2014 | Vlieghe et al. | |
| 9,084,771 B2 | 7/2015 | McAllister et al. | |
| 9,221,867 B2 | 12/2015 | Beliveau et al. | |
| 9,309,292 B2 | 4/2016 | Hong et al. | |
| 9,328,143 B2 | 5/2016 | Khrestchatisky et al. | |
| 9,611,323 B2 | 4/2017 | Dennis et al. | |
| 9,642,317 B2 | 5/2017 | Lewis et al. | |
| 9,656,981 B2 | 5/2017 | Spigelman et al. | |
| 9,675,654 B2 | 6/2017 | Parolaro et al. | |
| 9,676,849 B2 | 6/2017 | Farrington et al. | |
| 9,682,066 B2 | 6/2017 | Desai et al. | |
| 9,694,040 B2 | 7/2017 | Scialdone | |
| 2004/0039048 A1 | 2/2004 | Guzman Pastor et al. | |
| 2006/0235034 A1* | 10/2006 | Neamati | C07C 243/32 514/267 |
| 2009/0036363 A1 | 2/2009 | Lledo et al. | |
| 2014/0221469 A1 | 8/2014 | Ross et al. | |
| 2015/0313867 A1 | 11/2015 | Velasco Diez et al. | |
| 2015/0322149 A1 | 11/2015 | Bohrmann et al. | |
| 2016/0136127 A1 | 5/2016 | Liu et al. | |

FOREIGN PATENT DOCUMENTS

| | | |
|---|---|---|
| WO | 2009147439 | 12/2009 |
| WO | 2016030369 | 3/2016 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*
Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*

* cited by examiner

*Primary Examiner* — Jeffrey S Lundgren
*Assistant Examiner* — Chris E Simmons
(74) *Attorney, Agent, or Firm* — Ronald J. Richter; Hasse & Nesbitt

(57) ABSTRACT

A therapeutic method and composition which includes a cannabinoid chemically linked to a chemotherapy agent. The therapeutic composition is capable of crossing the blood-brain barrier, and delivery of the composition across the blood-brain barrier provides both chemotherapy for the treatment of brain cancer and alleviation of side effects caused by the chemotherapy agent. Once across the blood-brain barrier, the chemotherapy agent will be released to attack cancer cells, and the cannabinoid will be free to bind to cannabinoid receptors in the brain to alleviate side effects of chemotherapy such as nausea/vomiting, pain and decreased appetite.

10 Claims, 3 Drawing Sheets

DELIVERY OF A CHEMOTHERAPY AGENT ACROSS THE BLOOD-BRAIN BARRIER

FIELD OF THE INVENTION

The present invention relates in general to methods for delivering therapeutic compounds across the blood-brain barrier of patients, and more particularly to the use of cannabinoids coupled to a chemotherapy agent for transport across the blood-brain barrier.

BACKGROUND OF THE INVENTION

The mammalian brain is a complex and delicate organ which must operate within a highly secured environment. Not only is it sheltered from outside forces by the skull, but there is also an effective vascular protection system made of tightly wedged cells which make up the blood-brain barrier (BBB). The BBB was first characterized in 1885, when Paul Ehrlich injected dyes into live animals and observed that the brain was not stained blue like the rest of the body. The BBB protects the brain from pathogens, toxins and other insults, but represents a major obstacle to the delivery of drugs to the central nervous system (CNS). The BBB includes a vascular barrier (primarily capillary beds) and a blood-cerebrospinal fluid barrier (the choroid plexus), both of which are formed with a monolayer of endothelial cells cemented together by high-resistance intercellular tight junctions. Tight junctions seal the cells together so compounds and molecules must go through, rather than around, the endothelial cells. Tight junctions also restrict permeability between adjacent endothelial cells via polarized membrane proteins such as nutrient transporters. The BBB thus acts as a continuous blockade, preventing access of most blood-borne molecules, and only allowing entry of essential chemicals vital for CNS function.

Transport across the BBB typically occurs by one of the following means: lipid-mediated diffusion (lipophilic molecules only), carrier-mediated transport, receptor-mediated transcytosis, absorptive-mediated transcytosis or active transport. Although small, lipid-soluble agents can cross the BBB via diffusion through the capillary endothelial cells, they must have a sufficient amount of lipid solubility. Polar, water-soluble molecules enter the brain almost exclusively by carrier-mediated transport. Thus glucose, essential amino acids, glutamate, and most peptides (such as the naturally occurring enkephalins) which are polar and hydrophilic can only cross the BBB because a specific transport system is in place. If there is no such carrier, the BBB is a barrier that can be impossible to cross. Barrier permittivity of the BBB involves the surface activity of the molecule of interest, such as its hydrophobic and charged residues, as well as its relative size. The influence of the size of a compound or molecule on BBB penetration is generally inversely related to the square root of its molecular weight. In addition, the larger a compound is, the more difficult diffusion/entry will be no matter how beneficial its solubility characteristics are.

While physical properties such as low molecular weight and high lipid solubility both favor crossing the BBB by diffusion, passage through the BBB does not ensure that a compound will be pharmacologically effective. After passing through the monolayer of endothelial cells forming the BBB, the compound must then partition into the aqueous environment of the brain's interstitial fluid to exert an effect. As a result, a compound or molecule that is too lipid soluble can be sequestered by the capillary bed and not reach the cells behind the BBB. Lipid solubility also favors uptake by the peripheral tissues, which in turn lowers the concentration of the drug in blood. Thus, while the high lipid solubility of a specific compound can increase transport success across the BBB, it can also lower the amount of the compound presented to the brain. Even if the compound does manage to cross the BBB it may not arrive in a therapeutically relevant concentration, rendering it ineffective. Use of lipid solubility to improve drug delivery to the brain must thus find a balance between increased transport across the BBB and decreased amounts reaching the target tissue.

Additionally, the BBB is metabolically active and includes efflux transporters and enzymatic processes which play a large contributing role in final drug distribution. Several efflux transporters, such as the transmembrane protein P-glycoprotein (PGP), breast cancer resistance protein (BCRP), and multidrug resistance proteins (MRP) have profound clinical relevance to several CNS diseases such as cancers and HIV. Serving as a further defense to protect the brain, efflux transporter proteins can actively remove certain compounds or molecules that breach the BBB or they can deconstruct a compound or drug, making it inactive and rendering it useless.

In light of the above discussion, it is apparent that many hurdles must be overcome to successfully and effectively deliver a compound to the brain. A proposed treatment compound or molecule must be able to both cross the BBB and have a therapeutic effect within the brain. As a result, it is difficult to predict which compounds will penetrate the BBB to provide a therapeutic effect, and which will not. Most current brain-targeting therapies employ molecules that are either small enough or lipid-soluble enough to slip through the BBB in pharmacologically significant amounts. Further, attempts have been made to mimic lipid solubility. For example, U.S. Pat. No. 5,624,894 to Bodor describes placing a pharmacologically active peptide in a molecular environment which disguises its peptide nature by cloaking the polar ends of the peptide with lipophilic groups. The "lipidized" peptide is permitted unimpeded passive diffusion through the blood-brain barrier and into the brain capillaries. Several peptides have been successfully transported across the BBB that do not naturally show satisfactory BBB penetration, including two analgesics (a leucine-enkephalin analogue and kyotophin, an endogenous dipeptide) as well as a thyrotropin-releasing hormone analogue, which has potential applications for Alzheimer's disease and spinal cord injuries.

A number of approaches have been tried to overcome the challenges associated with drug delivery across the BBB, including disruption of the BBB, permeating the BBB, bypassing the BBB, or a combination thereof. Osmotic (e.g. using mannitol) and/or ultrasonic treatments can be used to temporarily disrupt the BBB, and many attempts have been made to utilize endogenous carrier proteins or synthetic "Trojan horses" (such as short amino acid chains or peptides) to "smuggle" drugs across the BBB. The BBB may be avoided entirely by direct injection of drugs into cerebrospinal fluid or directly into the brain. However, these methods present their own challenges such as ion imbalances, leaking neurotransmitters and release into the general circulation. While specific treatment regimens have benefitted from various measures devised to bypass the BBB, for many CNS treatment regimens the search for adequate brain delivery of a specific therapeutic compound or medicine continues. To date there is no unique vector that can be used as a universal brain delivery system.

*Cannabis* plants produce a group of biologically active chemicals called cannabinoids, which can produce mental and physical effects when consumed. A unique aspect of the BBB is that it allows cannabinoids to readily penetrate the BBB and bind with the brain's transmembrane cannabinoid receptors, $CB_1$ and $CB_2$. $CB_1$ is particularly abundant in the brain, while $CB_2$ is mainly expressed peripherally in the immune system. Cannabinoids mimic the action of anandamide, a naturally-occurring neurotransmitter. Anandamide is synthesized in areas of the brain controlling memory, motivation, higher thought processes, and movement control, and can affect one's appetite and reaction to pain. It may also help stop cancer cell proliferation, and exhibits both anti-anxiety and antidepressant properties. Anandamide, like all neurotransmitters, is metabolized quickly in the body. Cannabinoids which can bind to the same receptors as anandamide include cannabidiol (CBD), Δ-9-tetrahydrocannabinol (THC, the active ingredient in the prescription medication Marinol® (generic name dronabinol), 11-hydroxy-Δ-9-THC (a metaboloite of Δ-9-THC), cannabinol (CBN), Δ-8-THC, levonantradol, cannabivarin (CBDV), tetrahydrocannabivarin (THCV, a homologue of THC), cannabigerol (CBG), and acids and analogs thereof. It is now possible to synthesize many cannabinoids in the laboratory, eliminating the need to grow *Cannabis* for extraction of the naturally made compounds from its flowers.

Whole or crude marijuana (including marijuana oil or hemp oil) containing Δ-9-THC is regulated by the United States Drug Enforcement Administration (DEA) as a Schedule I Drug, ostensibly because it is a hallucinogen. The U.S. Food and Drug Administration (FDA) has not yet approved a drug product containing or derived from the whole *Cannabis* plant, even though *Cannabis* and *Cannabis*-derived products have been used by doctors to treat a number of medical conditions, such as AIDS wasting syndrome, epilepsy, neuropathic pain, treatment of spasticity associated with multiple sclerosis, and cancer and chemotherapy-induced nausea. Indeed, one of the most active areas of current research in the cannabinoid field is the study of the potential application of cannabinoids as therapeutic agents. Among these possible applications, cannabinoids have been known to exert palliative effects in cancer patients since the early 1970s. The best established of these effects is the inhibition of chemotherapy-induced nausea and vomiting.

Today, capsules of THC such as dronabinol (Marinol®, Syndros®) and synthetic cannabinoids such as nabilone (Cesamet®) are FDA-approved in the U.S., and also in several other countries for treating chemotherapy induced nausea and vomiting. In addition, medicinal use of Δ-9-THC is currently legal under state laws in many states, and THCV, a homologue of THC having a propyl (3-carbon) side chain instead of THC's pentyl (5-carbon) side chain, is currently being investigated for pharmaceutical purposes. THCV has been attracting a lot of attention because it is not regulated by the DEA and has potential in several medical applications. THCV has anti-anxiety, antioxidant, and neuroprotective properties, and has shown the ability to improve muscle control and reduce tremors in patients suffering from Alzheimer's and Parkinson's disease. THCV can also promote bone cell growth, regulate blood sugar levels, and suppress appetite.

Brain and spinal cord tumors are abnormal growths of tissue found inside the skull or the bony spinal column, which are the primary components of the central nervous system (CNS). The CNS is housed within rigid, bony quarters (i.e., the skull and spinal column), so any abnormal growth, whether benign or malignant, can place pressure on sensitive tissues and impair function. Tumors are classified according to the kind of cell from which the tumor seems to originate. Most primary malignant brain/CNS tumors are gliomas, caused by uncontrolled growth of glial cells which surround and support neurons. Gliomas can include (but are not limited to) astrocytoma, anaplastic astrocytoma, glioblastoma multiforme, oligodendroglioma, ependymoma, meningioma, lymphoma, schwannoma, and medulloblastoma. In a small number of individuals, primary tumors may result from specific genetic disease (e.g., neurofibromatosis, tuberous sclerosis) or from exposure to radiation or chemicals. The cause of most primary tumors remains a mystery.

Chemotherapy is a category of cancer treatment that uses strong drugs, typically administered orally or intravenously, to reduce or kill cancers and to prevent cancer cells from spreading to other parts of the body. While chemotherapy can be effective against cancer, it can also cause serious side effects, because the chemotherapy drugs which attack cancerous cells can also damage normal, healthy cells. Common chemotherapy-induced side effects include fever, chills, fatigue, insomnia, nausea/vomiting, sore mouth, diarrhea, constipation, loss of appetite leading to anorexia, pain or difficulty swallowing, swelling in the hands/feet, itching, shortness of breath, cough, muscle pain, and joint pain.

In general, cannabinoids can provide significant improvements in chemotherapy-induced side effects. Patients treated with THC and/or THCV have been shown to experience a higher quality of sleep and relaxation. The National Cancer Institute, an organization run by the U.S. Department of Health and Human Services, recognizes cannabinoids as an effective treatment for providing relief of a number of symptoms associated with cancer and chemotherapy treatments, including pain, nausea and vomiting, anxiety and loss of appetite. The American Cancer Society supports the need for more scientific research on cannabinoids for cancer patients, and recognizes the need for better and more effective therapies that can overcome the often debilitating side effects of cancer and its treatment. More specifically, one of the major cannabinoids found in *Cannabis*, cannabidiol (CBD), is effective at treating the more difficult to control symptoms of nausea, as well as preventing anticipatory nausea in chemotherapy patients. $CB_1$ agonists such as tetrahydrocannabivarin (THCV) and tetrahydrocannabinol (Δ-9-THC) are also effective at reducing conditioned rejection and chemotherapy-induced nausea. Cannabinoids can also significantly reduce neuropathic pain where traditional treatment has been unsuccessful, and without adversely affecting the efficacy of the chemotherapy, and can also help prevent weight loss and a loss of appetite in chemotherapy patients. Research also suggests that *Cannabis* may reduce the swelling in the hands and feet that can often occur with chemotherapy treatment. Cannabinoids have been shown to have anti-inflammatory properties, to be helpful in pain management, and to reduce inflammatory pain.

Most chemotherapy treatment regimens typically used on cancers originating in other organs employ compounds or molecules that are too large to penetrate the blood-brain barrier (BBB). As a result, most current chemotherapy drugs can only be delivered to the brain via surgical implantation, or injection into the cerebrospinal fluid (CSF). The present invention envisions using cannabinoids such as THC, CBD or THCV to improve delivery of a chemotherapy compound across the BBB to the brain, and is based on the premise that the ready passage of cannabinoids across the BBB while complexed with a chemotherapy agent can be used for treating cancers in the brain. It would therefore be advantageous to attach a cannabinoid such as THC, CBD or THCV to a known chemotherapy agent for improved transport across the blood-brain barrier and therapeutic effect. It would also be useful to safely deliver chemotherapy drugs directly across the blood-brain barrier while also providing cannabinoids to treat some of the debilitating side effects of the chemotherapy.

SUMMARY OF THE INVENTION

The present invention pertains to methods and compositions in which cannabinoids are attached to chemotherapy agents to improve delivery of the chemotherapy agent across the BBB to cause a therapeutic effect. Once across the BBB, the cannabinoid will attach to cannabinoid receptors in the brain (thereby alleviating nausea and pain, and increasing appetite) and the chemotherapy agent will be released to attack cancer cells.

A first aspect of the invention provides a therapeutic composition capable of crossing the blood-brain barrier, the composition comprising a chemotherapy agent for the treatment of brain cancer and a cannabinoid for alleviation of side effects caused by the chemotherapy agent, wherein the chemotherapy agent is chemically linked to the cannabinoid.

A second aspect of the invention provides a therapeutic composition for the treatment of brain cancer, the composition comprising: (a) a cannabinoid; and (b) a chemotherapy agent, wherein the cannabinoid and chemotherapy agent are chemically linked, and wherein the composition is capable of crossing the blood-brain barrier to provide both chemotherapy for the treatment of brain cancer and alleviation of side effects caused by chemotherapy.

A third aspect of the invention provides a method of treating a patient suffering from cancer of the brain, the method comprising administering to the patient a therapeutically effective amount of a composition comprising a cannabinoid and a chemotherapy agent, wherein the cannabinoid and chemotherapy agent are chemically linked, and wherein the composition is capable of crossing the blood-brain barrier to provide both chemotherapy for the treatment of brain cancer and alleviation of side effects caused by the chemotherapy agent.

The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

The present invention provides a method and composition for delivering a therapeutically effective amount of chemotherapy agent across the blood-brain barrier (BBB) of a patient with a cancer of the brain, such as a glioma. Further, the inventive composition provides a cannabinoid for treating the side effects of the chemotherapy agent.

A "therapeutically effective amount" as used herein means an amount sufficient to successfully cross the BBB and reach the target organ (i.e. brain tissue) in a subject suffering from a brain tumor or brain cancer.

As noted above, lipophilic cannabinoids such as tetrahydrocannabivarin (THCV), tetrahydrocannabinol (THC), and cannabidiol (CBD) are able to cross the blood-brain barrier (BBB). In fact, most cannabinoids are easily able to penetrate the blood-brain barrier. For example, the brain-to-blood ratio of THC levels in animals ranges from 1.6 in mice, to 2.0 in rats, 2.6 in pigs, and 3.0 in humans (measured in the tissues of human cadavers). Thus, THC levels are several times higher in the brain than in the blood. This is likely because the brain consists of very fatty tissue, and since THC is highly lipophilic, it makes sense that a high amount of the cannabinoid would settle in the brain. The brain-to-blood ratio of THCV in mice is even higher than THC, indicating that THCV will cross the BBB and settle in the brain at a higher rate than THC.

In contrast to cannabinoids, most chemotherapy drugs are not able to cross the BBB and can only be delivered to the brain via surgical implantation or injection into the CSF. The present invention envisions attaching chemotherapy drugs to cannabinoids via a linker or chemical bond, to deliver the chemotherapy drug across the BBB. Once the chemotherapy compound gains entry into the brain, the link/bond is metabolized and both the cannabinoid and the chemotherapy drug are released to fulfill their respective duties. The present invention thus provides a means to transport both a chemotherapy agent and a cannabinoid across the BBB in a timely manner to combat the brain cancer suffered by a patient, and to relieve the negative side effects of chemotherapy.

Figure 1:
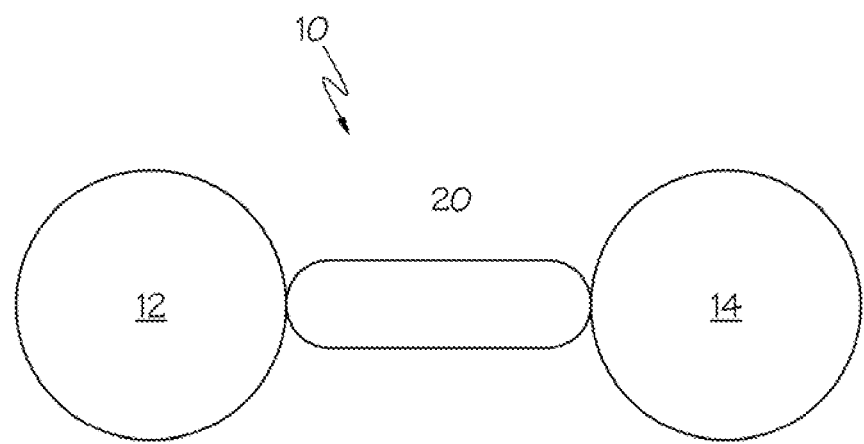
FIG. 1 illustrates a stylized perspective view of a cannabinoid-chemotherapy agent complex according to the present invention.

FIG. 1 schematically illustrates a cannabinoid-chemotherapy compound for the treatment of brain cancer, according to the present invention. The compound 10 typically includes a cannabinoid 12 such as THC, THCV, or CBD, joined via a chemical linker 20 to a chemotherapy agent 14 such as Carmustine, Lomustine, or Dacarbazine. In a preferred embodiment, THCV and Carmustine are combined to provide a THCV-Carmustine complex.

Carmustine (1,3-bis(2-chloroethyl)-1-nitrosourea), also known as "BiCNU" or "BCNU", is a nitrogen mustard nitrosourea compound used as an alkylating agent to treat several types of brain cancers. Carmustine causes a cytotoxic effect by alkylating and cross-linking DNA during all phases of the cell cycle, which disrupts DNA function, arrests the cell cycle, and leads to apoptosis. DNA repair enzymes are also inactivated by Carmustine. Lomustine (1-(2-chloroethyl)-3-cyclohexyl-1-nitrosourea), known as "CCNU" or "CeeNU", is also a highly lipid-soluble alkylating nitrosourea compound which readily crosses the blood-brain barrier and is used in chemotherapy for treating brain tumors. Dacarbazine, also known as imidazole carboxamide, is a low molecular weight chemotherapy medication used in the treatment of metastatic melanoma and Hodgkin's lymphoma.

While most chemotherapy agents do not cross the BBB, medications such as Carmustine and Lomustine are highly lipophilic and are able to cross the blood-brain barrier readily. Nevertheless, to improve the likelihood that the cannabinoid-chemotherapy agent complex will move beyond the BBB capillary beds after crossing the BBB, the cannabinoid (which is drawn to $CB_1$ receptors in the brain) and chemotherapy agent can be chemically linked, such that the cannabinoid (e.g. THCV) can assist as a transport vehicle, aiding the passive diffusion of the chemotherapy agent (e.g. Carmustine) portion of the complex across the blood-brain barrier and into the brain tissue. Once across the BBB, the complex is cleaved and the cannabinoid portion of the complex can bind with cannabinoid receptors in the brain, while the chemotherapy portion can be freed to attack cancer cells. Delivery of the inventive compound to the brain thus provides both anti-cancer activity and reduction in the side effects caused by the chemotherapy agent.

While chemotherapy agents such as Carmustine and Lomustine are highly lipophilic as noted above and thus readily able to cross the blood-brain barrier, when chemically linked with a cannabinoid such as THCV, concerns arise regarding passage of the complex across the BBB. The size and/or molecular weight of the compound, as well as the presence of hydrogen bonds and polar interactions between the cannabinoid 12 and the chemotherapy agent 14, may inhibit its passage at the tight junctions. As noted above, after passing through the monolayer of endothelial cells forming the BBB, the compound must then partition into the aqueous environment of the brain's interstitial fluid to exert an effect. As a result, a compound or molecule that is too lipid soluble can be sequestered by the capillary bed and not reach the cells behind the BBB. If the compound does manage to cross the BBB it may not arrive in a therapeutically relevant concentration, rendering it ineffective.

It is known in the art that a molecule or compound typically has a high probability of crossing the BBB if it has a mass of less than 500 Daltons and is able to form less than 8-10 hydrogen bonds. It is therefore notable that a proposed THCV-Carmustine complex has a molecular weight of approximately 488 Da and contains one hydrogen donor and seven hydrogen bond acceptors. More specifically, Carmustine is lipophilic and has a chemical formula of $C_5H_9Cl_2N_3O_2$; THCV is also lipophilic, is designed to cross the BBB to bind to cannabinoid receptors in the brain, and has a chemical formula of $C_{19}H_{26}O_2$. The coupled THCV-Carmustine complex thus has a chemical formula of $C_{24}H_{33}Cl_2N_3O_4$, less than 8-10 hydrogen bonds, and a molecular weight of approximately 488 Daltons. Thus the THCV-Carmustine complex has a small, lipophilic structure, putting it in the range of compounds that may cross the BBB.

Further, software is available that can provide predictive data for a specific molecular structure. Such software can provide calculations regarding lipid solubility, hydrogen bonding, pKa, absorption, distribution, metabolism, excretion and toxicity of a proposed compound or molecule. Such software can also provide the capability to design or modify structures to attain a desired property profile. For example, the chemical structure of the proposed THCV-Carmustine complex was entered into a program provided by Advanced Chemistry Development, (ACD/Labs), which specializes in research and development software for small molecule chemistry. Results showed that the physical properties of a THCV-Carmustine compound (i.e. weight, lipophilicity, and hydrogen bonding) are within the parameters given for a molecule that will cross the BBB, and that the proposed THCV-Carmustine complex is capable of "brain penetration sufficient for CNS activity." Further, using the same ACD/Labs software, proposed inventive complexes such as THCV-Lomustine, THC-Dacarbazine, THCV-Dacarbazine, and CBD-Dacarbazine all fall within the parameters favorable for penetration of the blood-brain barrier. While CBD and THC are larger molecules than THCV, the small Dacarbazine size places the cannabinoid-Dacarbazine complexes within favorable parameters for BBB penetration.

In addition to the fact that the inventive cannabinoid-chemotherapy complexes noted above all meet the physical parameters for molecular weight, lipophilicity, and hydrogen-bonding that will allow them to cross the BBB, the additional fact that they incorporate a compound (i.e. a cannabinoid) which has an active receptor (e.g. $CB_1$) in the brain can increase the likelihood that the cannabinoid-chemotherapy agent complex will move beyond the BBB capillary beds after crossing over. Once across the BBB and into the brain tissue, the cannabinoid portion is drawn to its receptors in the brain. It can be cleaved (e.g. by an amidine lyase enzyme, as discussed below) from the chemotherapy agent and then bind to the cannabinoid receptors in the brain. The chemotherapy agent (e.g. Carmustine), which prior to being cleaved from the cannabinoid was transported as part of the complex with the cannabinoid beyond the BBB capillary bed and into the brain tissue, is then free to attack cancer cells in the brain.

Figure 2:
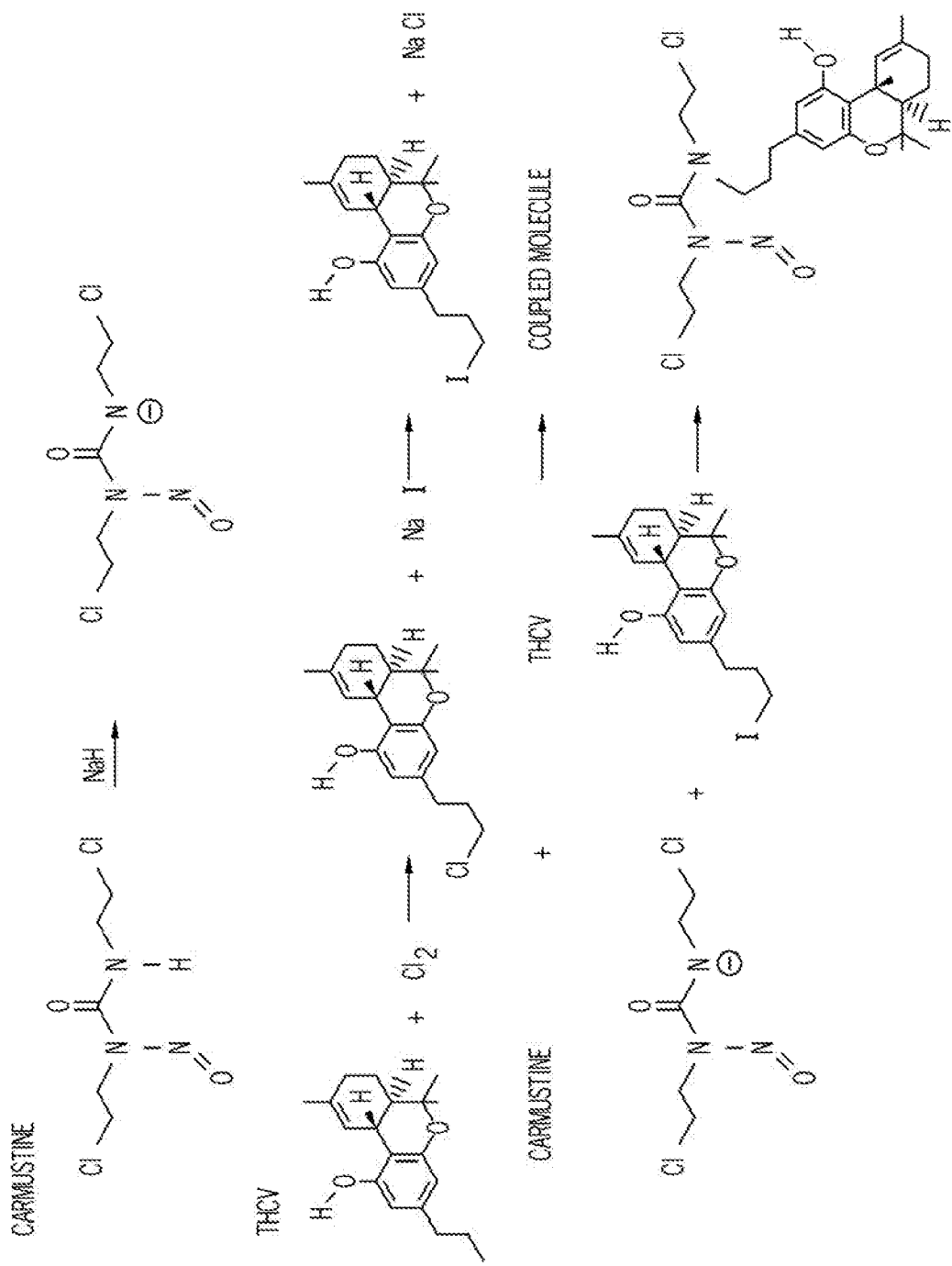
FIG. 2 illustrates one possible means in which the cannabinoid THCV can be combined with the chemotherapy agent Carmustine to produce a THCV-Carmustine complex in accordance with the present invention.

As illustrated in FIG. 2, a preferred embodiment of the inventive composition can be synthesized by linking Carmustine and THCV by a carbon-nitrogen bond. Through the small series of chemical reactions as illustrated, the molecular structures of Carmustine and THCV are coupled into a single compound, linked by a bond between a carbon atom on the THCV and a nitrogen atom on the Carmustine. More specifically, Carmustine can be initially reacted with sodium hydride (NaH) to make an intermediate Carmustine compound having a negative charge. THCV can be reacted with a halogen such as chloride ion to make an intermediate compound, which can then be reacted with sodium iodide (NaI) to make another THCV intermediate. Iodine is a better leaving group than chlorine, and replacing the chlorine atom with an iodine atom on the THCV molecule will cause it to readily react with the negatively charged intermediate Carmustine compound. The result is a stable complex in which Carmustine is chemically bonded to THCV. The chemical preparation of a THCV-Lomustine complex can follow the same steps.

While both Carmustine and THCV can cross the BBB individually, it is believed that the THCV-Carmustine complex can transport the Carmustine portion across the BBB faster than Carmustine alone. Cannabinoid compounds including THCV are drawn to and retained by cannabinoid receptors in the brain, such as the $CB_1$ receptor, once they gain access. Consequently, both the lipophilicity and the attraction to brain receptors by the THCV-Carmustine complex will help guarantee that the complex crosses the BBB and remains in the brain. Once the composition has crossed the BBB, it is cleaved and/or metabolized into its component parts. Specifically, the carbon-nitrogen bond linking Carmustine and THCV can be cleaved in vivo by an amidine lyase, which catalyses the release of amides or amidines by the cleavage of a carbon-nitrogen bond. Carmustine is then free to infiltrate the tumor, and the THCV can bind to the $CB_1$ receptor to exert its effects.

Figure 3A:
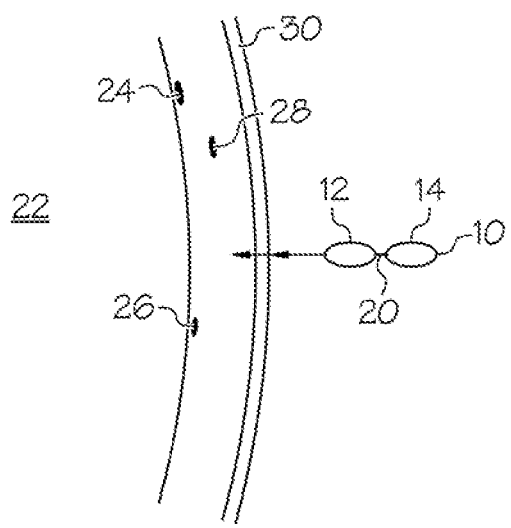
FIGS. 3A-3D illustrate successive views of the inventive THCV-Carmustine complex crossing the BBB and reaching the target area for treatment.
Figure 3B:
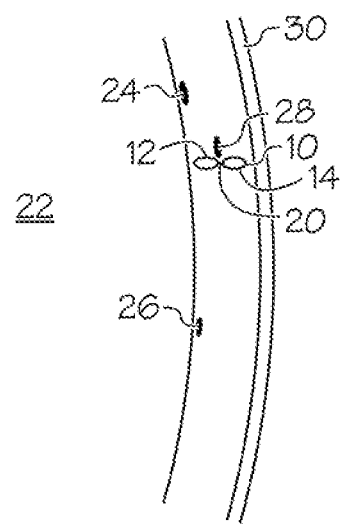
Figure 3C:
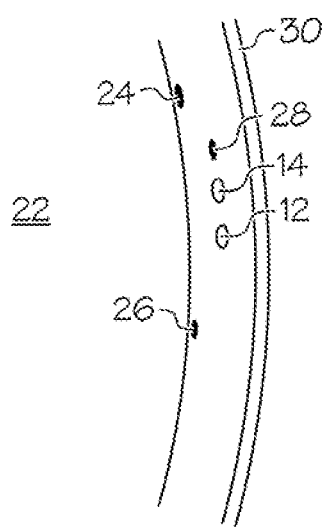
Figure 3D:
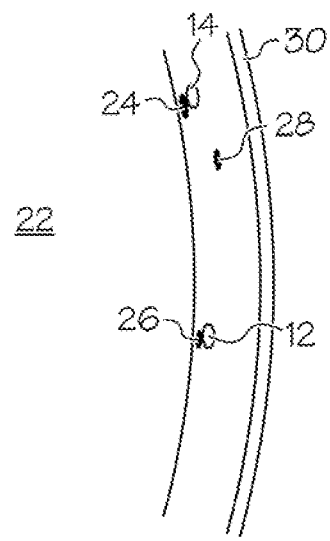

FIGS. 3A-3D illustrate how a THCV-Carmustine complex can cross the BBB and then be cleaved so that the component parts can exert a therapeutic effect in the brain. Specifically, FIG. 3A illustrates the THCV-Carmustine complex 10 crossing the BBB 30 and moving beyond the BBB capillary bed, drawn to the brain's cannabinoid receptors. FIG. 3B illustrates brain tissue 22 which includes both a tumor or lesion 24 and cannabinoid receptors 26 (e.g., $CB_1$). The amidine lyase 28 reacts with the THCV-Carmustine complex 10 to break the carbon-nitrogen bond 20. FIG. 3C illustrates the THCV portion 12 and the Carmustine portion 14 as separate molecules and the amidine lyase 28 available for other reactions. FIG. 3D illustrates migration of the Carmustine molecule 14 to the brain lesion 24 and the THCV molecule 12 migrating for attachment to brain cannabinoid receptors 26 ($CB_1$).

Many pharmaceutical dosages are administered in the form of pills, granules, powders, and liquids. The inventive composition can be formulated as is known in the art to be administered to the patient in the form of a pill, a liquid, a granule, a powder, an orally dissolving (sublingual) tablet, on oral film, a mucoadhesive strip, chewing gum, a vaporizer, an inhaler, etc. Generally, a pill design is for swallowing intact or chewing to deliver a precise dosage of medication to patients. The pills, which include tablets and capsules, are able to retain their shapes under moderate pressure. However, some patients, particularly pediatric, geriatric, and cancer patients, have difficulty swallowing or chewing solid dosage forms. Many such patients are unwilling to take these solid preparations due to fear of choking. Hence, orally dissolving tablets and oral film drug delivery can be a better alternative in such cases. The oral availability of many drugs is poor because of the pH of the stomach, the presence of enzymes, and extensive first-pass metabolism. Traditionally, these drugs have been administered as parenteral drug delivery systems, which invariably lead to poor patient compliance. This has made the pharmaceutical industry look for alternative routes of drug delivery like film drug delivery. Oral film may be a fast dissolving film or a sustained release oral film. Inhalers and vaporizers are also useful to bypass the stomach.

While the present invention has been illustrated by the description of embodiments thereof in considerable detail, it is not intended to restrict or limit the scope of the appended claims to such detail. Additional advantages and modifications will be readily apparent to those skilled in the art. Departures may be made from such details without departing from the scope of the invention.

What is claimed is:

1. A therapeutic composition capable of crossing the blood-brain barrier, the composition comprising a chemotherapy agent for the treatment of brain cancer and a cannabinoid for alleviation of side effects caused by the chemotherapy agent, wherein the chemotherapy agent is chemically linked to the cannabinoid, and wherein the cannabinoid is tetrahydrocannabivarin and the chemotherapy agent is Carmustine.

2. The composition of claim 1, wherein the chemical link between tetrahydrocannabivarin and Carmustine is cleavable after crossing the blood-brain barrier, thereby allowing tetrahydrocannabivarin to bind to cannabinoid receptors in the brain and the Carmustine to attack cancer cells.

3. The composition of claim 1, wherein the brain cancer is glioblastoma multiforme.

4. The composition of claim 1, wherein the side effect caused by the chemotherapy agent is nausea.

5. The composition of claim 1, wherein the composition is formulated to be administered in the form of an inhaler.

6. A therapeutic composition for the treatment of brain cancer, the composition comprising:
   a. a cannabinoid; and
   b. a chemotherapy agent, wherein the cannabinoid and the chemotherapy agent are chemically linked, wherein the composition is capable of crossing the blood-brain barrier to provide both chemotherapy for the treatment of brain cancer and alleviation of side effects caused by chemotherapy, and wherein the cannabinoid is tetrahydrocannabivarin and the chemotherapy agent is Carmustine.

7. The composition of claim 6, wherein the chemical link between tetrahydrocannabivarin and Carmustine is cleavable after crossing the blood-brain barrier, thereby allowing tetrahydrocannabivarin to bind to cannabinoid receptors in the brain while also allowing the Carmustine to attack cancer cells.

8. The composition of claim 6, wherein the brain cancer is glioblastoma multiforme.

9. The composition of claim 6, wherein the side effect caused by the chemotherapy agent is nausea.

10. The composition of claim 6, composition is formulated to be administered in the form of an inhaler.

* * * * *

UNITED STATES PATENT AND TRADEMARK OFFICE
CERTIFICATE OF CORRECTION

PATENT NO. : 10,688,191 B2
APPLICATION NO. : 15/875114
DATED : June 23, 2020
INVENTOR(S) : Heidi Rowles Page 1 of 1

It is certified that error appears in the above-identified patent and that said Letters Patent is hereby corrected as shown below:

In the Claims

Claim 10, Column 10, Line 38, delete "claim 6, composition" and Insert --claim 6, wherein the composition--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*